United States Patent
Otaki et al.

(10) Patent No.: US 7,092,151 B2
(45) Date of Patent: Aug. 15, 2006

(54) MICROSCOPE HAVING A PIPETTE DEVICE

(75) Inventors: Tatsuro Otaki, Edogawa-ku (JP); Yoshitaro Nakano, Sunto-gun (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 10/889,063

(22) Filed: Jul. 13, 2004

(65) Prior Publication Data

US 2005/0012990 A1    Jan. 20, 2005

(30) Foreign Application Priority Data

Jul. 15, 2003 (JP) ............................. 2003-196880

(51) Int. Cl.
    *G02B 21/00* (2006.01)
(52) U.S. Cl. ...................... 359/368; 359/387
(58) Field of Classification Search ................ 359/368, 359/385, 387, 389
    See application file for complete search history.

(56) References Cited

U.S. PATENT DOCUMENTS

| 3,680,947 | A | * | 8/1972 | Wanesky ..................... 359/393 |
| 4,270,838 | A | * | 6/1981 | Furusawa et al. ........... 359/385 |
| 4,367,914 | A | * | 1/1983 | Mukasa ....................... 359/385 |
| 4,749,270 | A | * | 6/1988 | Endo et al. .................. 359/392 |
| 4,920,053 | A | * | 4/1990 | Inoue et al. .................. 435/30 |
| 5,276,324 | A |   | 1/1994 | Ohtaki et al. |
| 5,808,790 | A |   | 9/1998 | Otaki et al. |
| 6,411,433 | B1 | * | 6/2002 | Miyoshi ....................... 359/396 |
| 6,621,079 | B1 | * | 9/2003 | Shao et al. .................. 250/306 |

FOREIGN PATENT DOCUMENTS

| JP | A 5-40009 | 2/1993 |
| JP | A 9-203864 | 8/1997 |
| JP | A 2001-117009 | 4/2001 |

* cited by examiner

*Primary Examiner*—Mark A. Robinson
(74) *Attorney, Agent, or Firm*—Oliff & Berridge, PLC

(57) ABSTRACT

A well plate holding a specimen to be observed is placed on a fixed stage, and the specimen is observed through an objective lens disposed below the well plate. A well set on the optical axis is illuminated through transmitted illumination provided by a transmitted illumination device. The transmitted illumination device includes a plurality of LEDs disposed to form a ring shape, and a through hole is formed further inward relative to the LEDs. When injecting a reagent into the well being observed, the reagent is drawn by using a head at a pipette device, and then the head is moved to a point above the well being observed through the hole formed at the transmitted illumination device.

11 Claims, 4 Drawing Sheets

MICROSCOPE HAVING A PIPETTE DEVICE

INCORPORATION BY REFERENCE

The disclosure of the following priority application is herein incorporated by reference:

Japanese Patent Application No. 2003-196880 filed Jul. 15, 2003

BACKGROUND OF THE INVENTION

1. Field of the Invention

The present invention relates to a microscope and more specifically relates to a microscope having a pipette.

2. Description of the Related Art

Japanese Laid Open Patent Publication No. 2001-117009 discloses an inverted microscope having an objective lens disposed under a specimen stage, in which the specimen is observed from below through the bottom surface of a well plate placed on the stage. In this type of inverted microscope, epi-illumination, whereby the illuminating light is radiated from the objective lens onto the specimen, is adopted in fluorescence observation and transmitted illumination is adopted in bright field observation, phase contrast observation and the like.

When observing an biological specimen with a microscope, a reagent or the like may be individually injected onto the specimen placed inside wells during the observation. In such a situation, an automatic pipette is often utilized to inject the reagent into numerous wells accurately and efficiently.

However, when the specimen is illuminated through transmitted illumination, as in bright field observation or phase contrast observation, the well plate is illuminated from a position above the specimen, and as a result, the pipette used to inject the reagent onto the specimen and the transmitted illumination device will interfere with each other. Accordingly, the illumination device is moved off the optical axis when injecting the reagent into the individual wells, and once the injection is completed, the illumination device is reset above the specimen. Since the specimen cannot be illuminated during the injection, a problem arises in that any change occurring in the specimen while the reagent is being injected onto the specimen cannot be observed.

SUMMARY OF THE INVENTION

A microscope according to the present invention comprises: a stage on which a specimen container containing a specimen is placed; an illumination device that illuminates the specimen; an objective lens that forms an observation image by condensing light from the specimen illuminated with the illumination device; a pipette device that injects a liquid into the specimen container; a moving device that moves the pipette device; and an opening formed at the illumination device, that enables movement of the pipette device. It is preferable that the moving device moves the pipette device between an injecting position at which the pipette device is engaged to inject the liquid into the specimen container and a retracted position at which the pipette device is not engaged in liquid injection.

A microscope according to the present invention comprises: a stage on which a specimen container containing a specimen is placed; an illumination device disposed above the specimen, that illuminates the specimen; an objective lens disposed below the specimen, that forms an observation image by condensing light from the specimen illuminated with the illumination device; a pipette device that injects a liquid into the specimen container; a moving device that moves the pipette device between an injecting position at which the pipette device is engaged to inject the liquid into the specimen container and a retracted position at which the pipette device in not engaged in liquid injection; and an opening formed at the illumination device, that enables movement of the pipette device.

It is possible that the illumination device includes a plurality of light sources disposed to form a substantially ring shape along a circumference of a circle centering around an optical axis of the objective lens; and the opening is formed in an area that contains the optical axis and is surrounded by the plurality of light sources.

It is also possible that the illumination device includes a plurality of light sources disposed to form a substantially ring shape along a circumference of a circle centering around an optical axis of the objective lens; and the opening is formed with an area containing the optical axis and surrounded by the plurality of light sources and a portion of the circle centering around the optical axis.

It is possible that the illumination device includes a plurality of light sources disposed over an entire area within a circle centering around an optical axis of the objective lens; and the opening is formed at an area inside the circle, which contains the optical axis.

It is also possible that the illumination device includes a first light source group having a plurality of light sources disposed to form a substantially ring shape along a circumference of a circle centering around an optical axis of the objective lens and a second light source group having a plurality of light sources disposed further inward relative to the first light source group; the opening is formed at an area containing the optical axis and surrounded by the second light source group; and the microscope further comprises an illumination control unit that switches over between a first illumination mode in which the first light source group is turned on and the second light source group is turned off and a second illumination mode in which both the first light source group and the second light source group are turned on.

It is possible that the illumination device includes a first light source group having a plurality of light sources disposed to form a substantially ring shape along a circumference of a circle centering around an optical axis of the objective lens and a second light source group having a plurality of light sources disposed further inward relative to the first light source group; the opening is formed with a portion of an area containing the optical axis in which the second light source group is to be disposed and a portion of an area in which the first light source group is to be disposed; and the microscope further comprises an illumination control unit that switches over a first illumination mode in which the first light source group is turned on and the second light source group is turned off and a second illumination mode in which both the first light source group and the second light source group are turned on.

A phase plate disposed in the vicinity of a pupil of the objective lens may be further comprised; and the plurality of light sources may be disposed at a position optically conjugate with the phase plate.

DESCRIPTION OF THE PREFERRED EMBODIMENT

The following is an explanation of an embodiment achieved according to the present invention, given in reference to the drawings.

Figure 1:
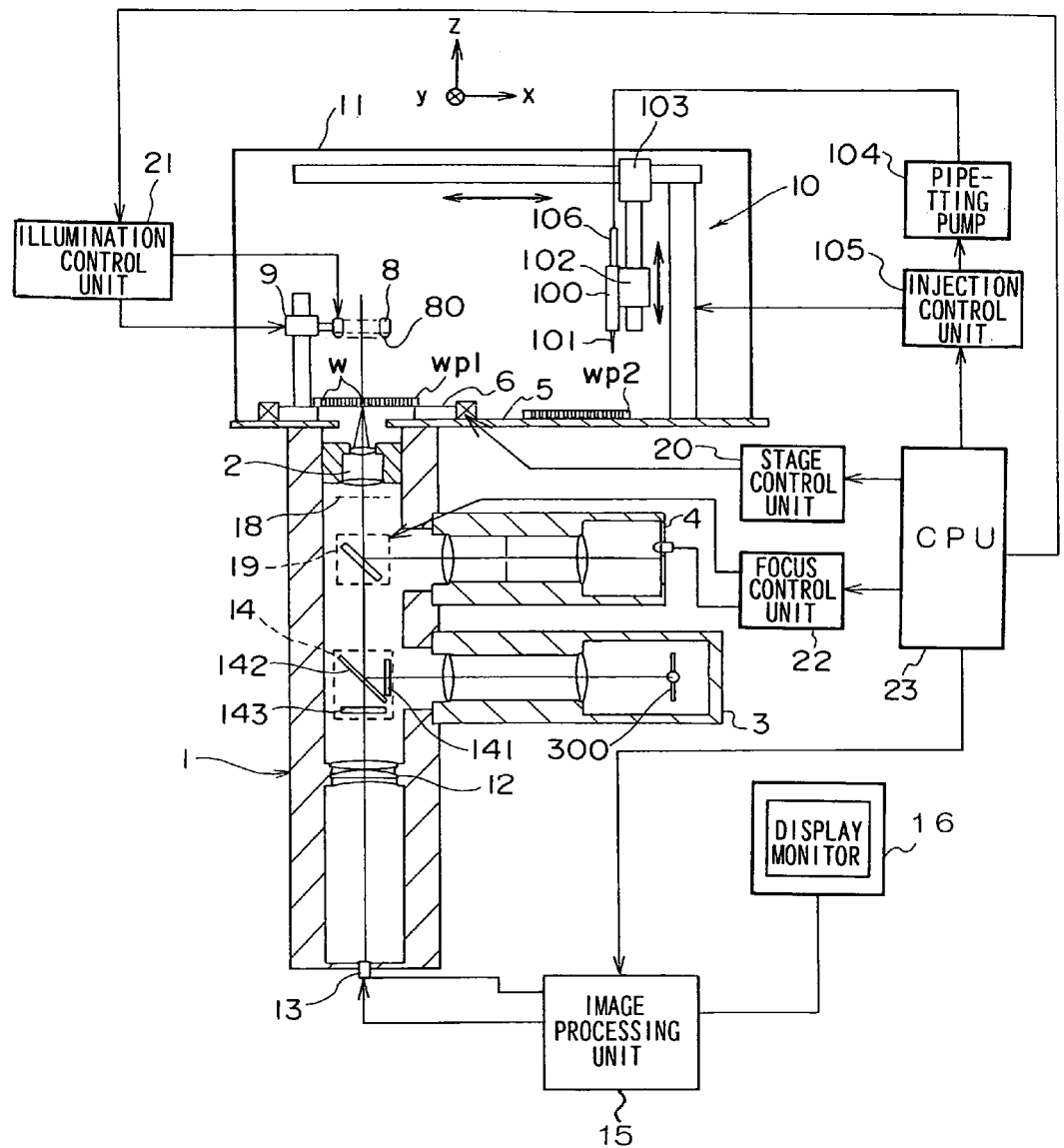
FIG. 1 shows the structure adopted in an embodiment of a microscope according to the present invention.

FIG. 1 schematically shows the structure of a microscope achieved in the embodiment of the present invention, which is realized as a an inverted microscope having a pipette.

When a biological specimen such as live cells in a solution is to be observed in a large quantity by using a microscope, a well plate is often used as a specimen container. At a well plate, numerous small wells assuming a cylindrical shape are formed in a lattice pattern and a culture solution used to culture cells or the like is placed within the wells. The specimen in such a well plate is normally observed by using an inverted microscope because of the ease of observation that inverted microscopes afford. It is to be noted that while epi-illumination whereby the illuminating light is radiated from the objective lens onto the specimen is adopted when the specimen is observed in fluorescence observation, transmitted illumination is adopted to observe the specimen in bright field observation or phase contrast observation in the inverted microscope.

As shown in FIG. 1, an epi-illumination device 3 and an autofocus device 4 are disposed at a microscope main body 1 having an objective lens 2. An observation light flux originating from the objective lens 2 forms an image through an image forming lens 12, and the resulting observation image is captured by an image-capturing element 13 which may be constituted of a CCD.

In addition, atop the microscope main body 1, a fixed stage 5 on which a specimen is placed is provided. An xyz stage 6, which is allowed to move along three axes, an x axis, a y axis and a z axis, is disposed on the fixed stage 5, and a well plate WP1 used as a specimen container is placed on the xyz stage 6. The drive of the xyz stage 6 is controlled by a stage control unit 20. At the well plate WP1, numerous wells W are formed in a lattice pattern, and a well W to be observed is set on the optical axis by moving the xyz stage 6 along the x direction and the y direction.

A transmitted illumination device 8 which is used for transmitted illumination of the specimen is provided above the xyz stage 6, and the transmitted illumination device 8 is caused to move up/down by a vertical position adjustment device 9. An illumination control unit 21 implements on/off control of the transmitted illumination device 8 and drive control of the vertical position adjustment device 9.

In addition, a pipette device 10 used to individually inject a reagent or the like into the wells W at the well plate WP1 set on the xyz stage 6 is provided on the fixed stage 5. The pipette device 10 includes a head 100 having a nozzle 101 through which the reagent is injected into the individual wells, a z drive unit 102 which moves the head 100 up/down, an xy drive unit 103 which moves the head 100 along the x and y directions, a pipetting pump 104 used to draw in and inject the reagent and a control unit 105 that controls the drive of the pipetting pump 104, the z drive unit 102 and the xy drive unit 103. The head 100 is connected to the pipetting pump 104 through a tube 106.

In this document, the head 100 and the nozzle 101 are collectively referred to as a pipette used to inject a liquid such as a reagent into the specimen container (the well plate WP 1).

Inside wells formed at a well plate WP2 set on the fixed stage 5, the reagent to be injected onto the specimen to be observed is placed, and the pipette device 10 is employed to inject the reagent into the individual wells W at the well plate WP1. It is to be noted that the fixed stage 5 is covered with a casing 11 which keeps the temperature and the moisture content of the specimen at constant levels and also functions as a black box. The xyz stage 6, the head 100 of the pipette device 10, the z drive unit 102, the xy drive unit 103 and the like are housed inside the casing 11

When the specimen is fluoresced for observation by engaging the epi-illumination device 3, a filter block 14 is inserted on the optical axis as shown in FIG. 1. At the filter block 14, an excitation filter 141, a dichroic mirror 142 and a barrier filter 143 are disposed. Light within a predetermined wavelength range, which is contained in the light generated at a light source 300 in the epi-illumination device 3, is transmitted through the excitation filter 141 as excitation light. The excitation light is then reflected at the dichroic mirror 142 and illuminates the specimen set on the optical axis via the objective lens 2.

The specimen to undergo fluorescence observation will have already been dyed with a reagent containing a fluorescent substance, and as excitation light is radiated onto the specimen, fluorescent light is generated. The fluorescent light thus generated first travels through the objective lens 2 and then it is transmitted through the dichroic mirror 142. Subsequently, any superfluous light is eliminated through the barrier filter 143 and the image forming lens 12 forms an image on the image-capturing element 13 by using only the necessary fluorescent light. An image capturing signal output from the image-capturing element 13 is then processed at an image processing unit 15, and a microscope image is displayed at a display monitor 16.

In addition, when the specimen is observed through bright field observation or phase contrast observation by engaging the transmitted illumination device 8, the filter block 14 for fluorescent observation is retracted and set outside the optical path. It is to be noted that when observing the specimen in phase contrast observation, an objective lens 2 having a phase plate 18 disposed in the vicinity of the pupil position of the objective lens 2 should be utilized. When such an objective lens 2 is used, the vertical position of the transmitted illumination device 8 should be adjusted with the vertical position adjustment device 9 so as to set the z position of the transmitted illumination device 8 to a point which is conjugate with the pupil position of the objective lens 2. Namely, when observing the specimen in phase contrast observation, the transmitted illumination device 8 should be set to a position optically conjugate with the position of the phase plate 18 along the z direction.

When automatically adjusting the focal point by engaging the autofocus device 4, a mirror 19 is inserted on the optical axis to guide the light flux from the specimen to the autofocus device 4. The focal adjustment is achieved by moving the xyz stage 6 along the optical axis (along the z direction) and thus adjusting the distance between the specimen and the objective lens 2. A focus control unit 22 controls the autofocus device 4, whereas a CPU 23 implements overall control of the microscope.

Figure 2:
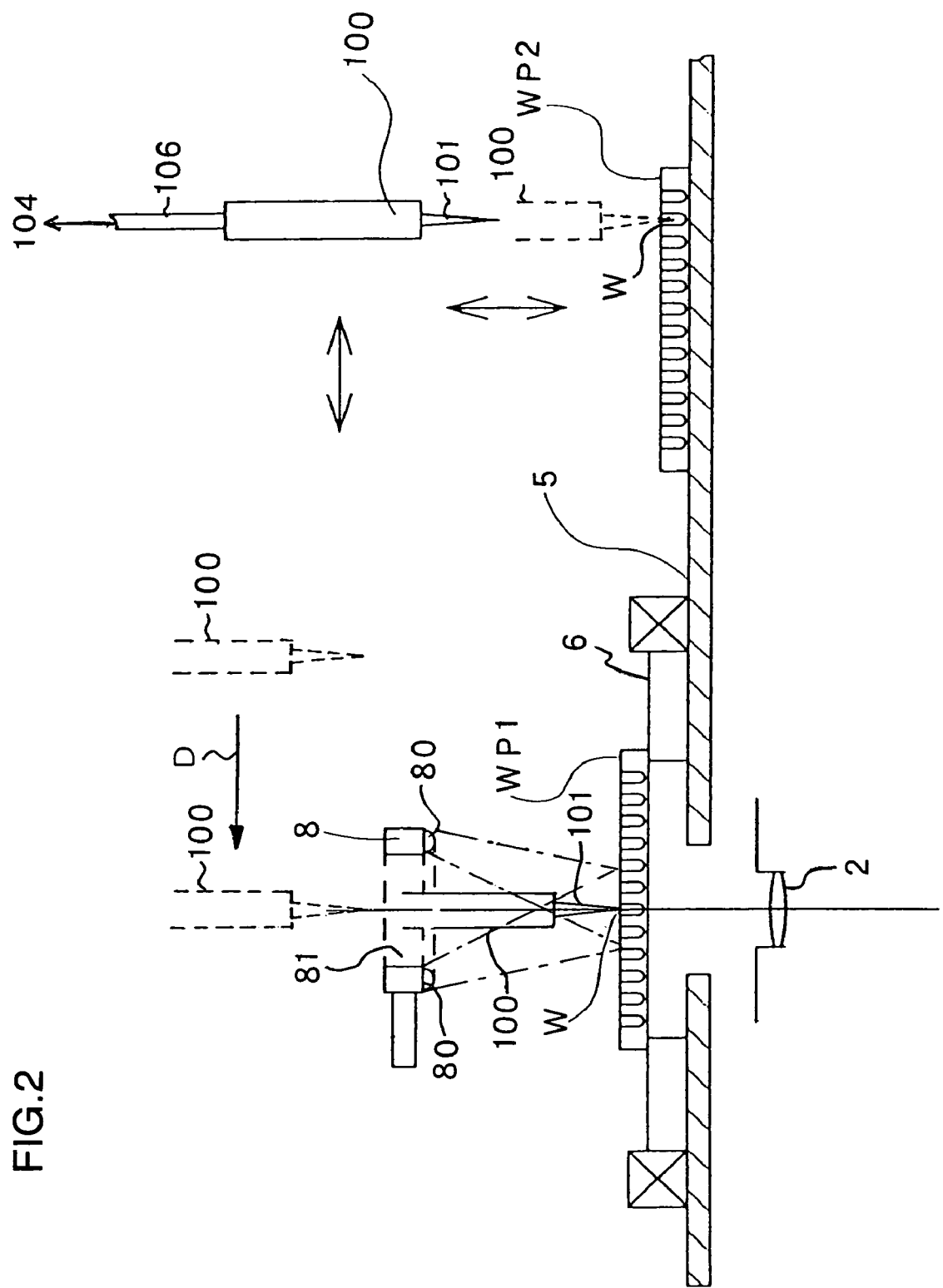
FIG. 2 illustrates the injection operation of a pipette device.
Figure 3A:
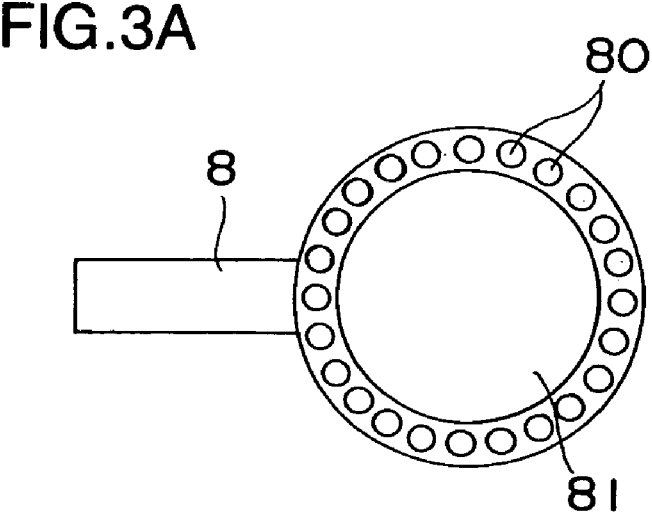
FIGS. 3A to 3C present examples of transmitted illumination devices.

FIG. 2 illustrates the injection operation of the pipette device 10. For instance, when observing the specimen through bright field observation or phase contrast observation in the microscope, the specimen is illuminated with the transmitted illumination device 8. FIG. 3A is a plan view of the transmitted illumination device 8, viewed from the side on which the objective lens 2 is present. The transmitted illumination device 8 in FIG. 3A, which is suited for phase contrast observation, has a plurality of light emitting diodes (LEDs) 80 disposed in a substantially ring shape along the circumference of a circle at the center of which the optical axis of the objective lens 2 extends. A hole (opening) 81 which passes through from the top to the bottom in the z direction is formed at the round central area where no LEDs 80 are disposed.

In phase contrast observation, illuminating light such as light from a halogen lamp is normally radiated onto the specimen via a ring-shaped slit. By using light sources disposed to form a ring shape, as in the transmitted illumination device 8 shown in FIG. 3A, it becomes possible to achieve similar illumination without having to use a ring-shaped slit. As shown in FIG. 2, the individual LEDs 80 are set at a tilt toward the optical axis so as to irradiate the well W set on the optical axis.

In order to inject the reagent during the observation, the head 100 of the pipette device 10 is first lowered and the nozzle 101 is inserted into one of the wells W at the reagent well plate WP2. Then, the reagent in the well W is drawn into the nozzle 101 with the pipetting pump 104 (see FIG. 1). Once the reagent is drawn into the nozzle 101, the head 100 is raised and is caused to make a parallel movement toward the transmitted illumination device 8, as indicated by the arrow D in FIG. 2. When the head 100 is aligned at the center of the hole 81 of the transmitted illumination device 8, i.e., when the head 100 is aligned with the optical axis of the objective lens 2, the parallel movement is stopped. Subsequently, the head 100 is lowered and the reagent is injected into the well W at the well plate WP1, which is currently being observed. Once the injection is completed, the head 100 is moved and is reset to the position above the well plate WP2 by reversing the earlier movement.

It is to be noted that the position to which the head 100 is lowered through the center of the hole 81 in order to inject the reagent into the well W as shown in FIG. 2 is referred to as the injection position at which the liquid is injected into the well W. In addition, a position assumed when the head 100 is not engaged in the operation for injecting the liquid into the well W is referred to as a retracted position.

Since the well W set on the optical axis is illuminated with the LEDs 80 of the transmitted illumination device 8, the specimen in the well W can be observed through the microscope even during the reagent injection as shown in FIG. 2. As a result, any change occurring in the specimen cells can be observed during or before and after the reagent injection. While the LEDs 80 are disposed over the entire circumference of the circle with the optical axis of the objective lens 2 extending along the center thereof in the example illustrated in FIG. 3A, a notched portion 82 may be formed as in a transmitted illumination device 8B shown in FIG. 3B.

Figure 3B:
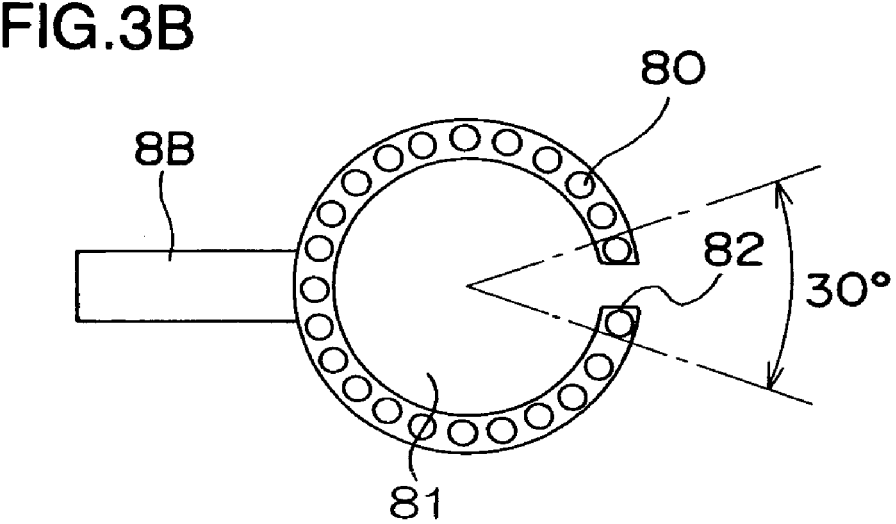

In the example presented in FIG. 3B, the notched portion 82 ranges over an area corresponding to a single LED. This notched portion 82 is formed in the transmitted illumination device 8B at a position facing opposite the pipette device 10. In this case, the head 100 may make a parallel movement toward the center of the hole 81 so as to allow the nozzle 101 to pass through the notched portion 82. In such a case, the distance over which the head 100 needs to move vertically can be reduced and the length of time required for the injecting operation is thus reduced. It goes without saying that if the width of the notched portion 82 is greater than the external diameter of the head 100, the head 100 itself may pass through the notched portion 82.

The illumination device 8B having the notched portion 82 formed therein, as shown in FIG. 3B, may be utilized for phase contrast observation as long as the angular range a of the notched portion 82 is up to approximately 30° relative to the center of the hole 81. It is to be noted that bright field observation can be conducted with ring-shaped illuminating light such as the illuminating light provided by the transmitted illumination device 8 or 8B.

Figure 3C:
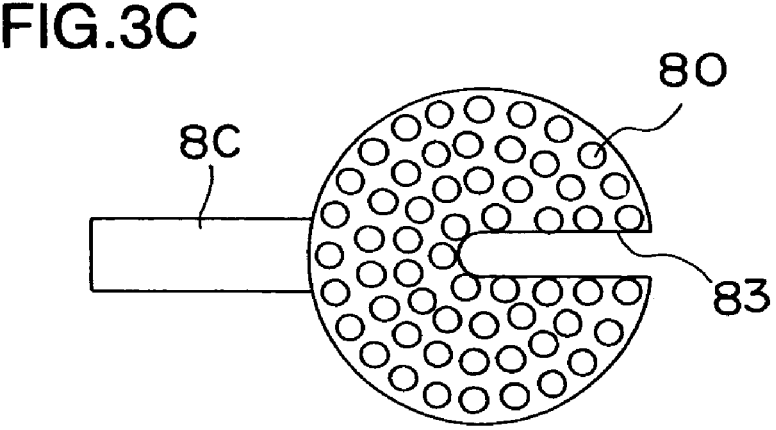
Figure 4A:
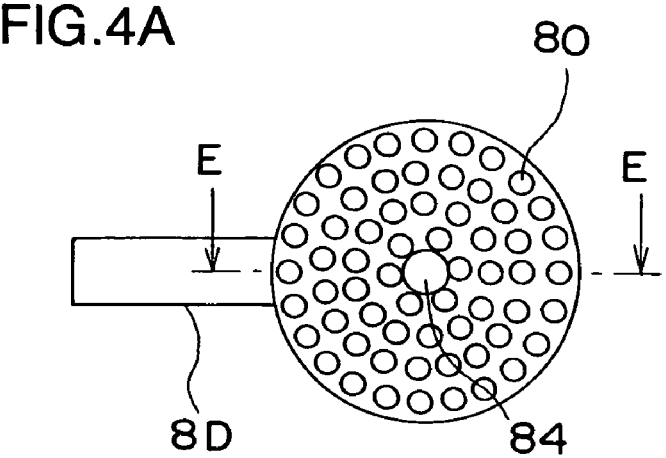
FIG. 4A is a plan view of an example of a transmitted illumination device.

Alternatively, either of transmitted illumination devices 8C and 8D shown in FIGS. 3C and 4A may be utilized instead of the transmitted illumination device 8 or 8B in FIG. 3A or 3B. The transmitted illumination device 8C in FIG. 3C includes LEDs 80 over the entire disk-shaped area centered around the optical axis of the objective lens 2. The disk at which the LEDs 80 are disposed has a notched portion 83 which extends from the periphery of the disk to the center of the transmitted illumination device 8C, i.e., to the area containing the optical axis of the objective lens 2. The transmitted illumination device 8D shown in FIG. 4A, on the other hand, includes LEDs 80 disposed over the entire surface of the disk centering around the optical axis of the objective lens 2. At the disk at which the LEDs 80 are disposed, a through hole 84 is formed at a central area of the transmitted illumination device 8D, i.e., at an area containing the optical axis of the objective lens 2.

Figure 4B:
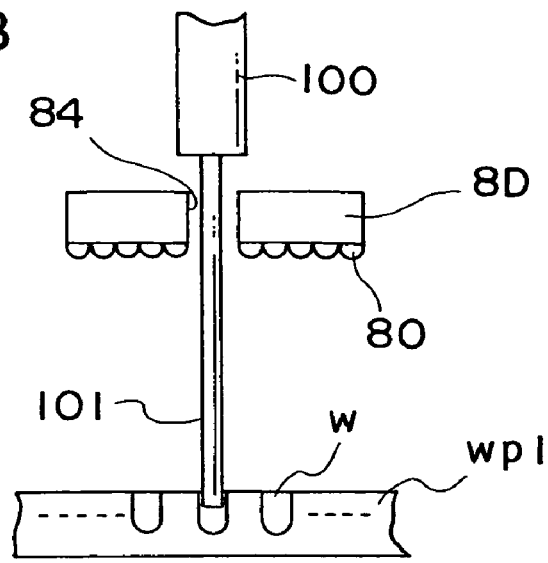
FIG. 4B is a sectional view of the transmitted illumination device during an injection operation and FIG. 4C shows the transmitted illumination device during a phase contrast observation.

When the transmitted illumination device 8C is utilized, the head 100 is moved to engage in the injecting operation as the head 100 is moved in conjunction with the transmitted illumination device 8B. In conjunction with the transmitted illumination device 8D, the entire length of the nozzle 101 should be increased as shown in FIG. 4B if the internal diameter of the hole 84 is smaller than the external diameter of the head 100, so as to allow the nozzle 101 to be inserted into the well W through the hole 84. It is to be noted that since the external diameter of the nozzle 101 is only approximately several millimeters, the internal diameter of the hole 84 only needs to be as large as the dimension of a single LED. It is to be noted that FIG. 4B is a sectional view taken along E—E in FIG. 4A.

Figure 4C:
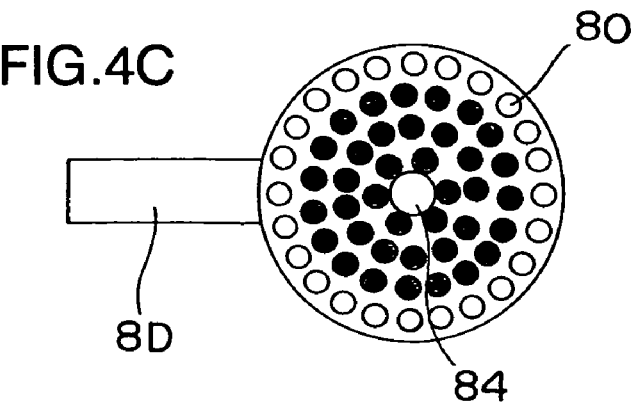

The transmitted illumination devices 8C and 8D having LEDs 80 disposed over almost the entire range of the circular area are more suited for providing illumination for bright field observation than the ring-shaped transmitted illumination devices 8 and 8B. In addition, when conducting a phase contrast observation, only the LEDs 80 disposed on the outermost edge (a first light source group) are turned on and the LEDs 80 disposed further inward (a second light source group) are turned off, as shown in FIG. 4C. Consequently, illuminating light identical to the illuminating light provided by the ring-shaped transmitted illumination device 8 is achieved to enable phase contrast observation. It goes without saying that LEDs 80 disposed on an inner circle relative to the first light source group may be turned on to be used in phase contrast observation, instead.

The illumination mode suited for phase contrast observation achieved by turning on the first light source group and turning off the second light source group is referred to as a first illumination mode. The illumination mode suited for bright field observation achieved by turning on both the first light source group and the second light source group is referred to as a second illumination mode. The transmitted illumination device is switched to the first illumination mode or the second illumination mode by the illumination control unit 21. It is to be noted that when using the transmitted illumination device 8C, too, phase contrast observation or bright field observation is conducted by controlling on/off of a plurality of LEDs 80 in a similar manner.

While the LEDs 80 are used as the light sources in the embodiment described above, any of various other light sources may be used instead of LEDs. In addition, the present invention may be adopted in a microscope in which the observation image of the specimen is seen through an eyepiece lens as well as in the microscope in which the observation image is captured with the image-capturing element 13.

Furthermore, no restrictions whatsoever are imposed by the embodiment described above on the implementation of the present invention, as long as the features characterizing the present invention are not compromised. The LEDs disposed at the illumination device 8 may assume an arrangement other than those described in reference to the embodiment. For instance, while FIGS. 3A and 3B show examples in which LEDs 80 are disposed in a single row along the circumference of the circle centered around the optical axis of the objective lens 2, LEDs 80 may be disposed along two or three rows, instead. In addition, as long as the liquid injecting operation of the pipette device 10 is facilitated, the size of the opening is not limited to those in the examples presented in FIGS. 3A through 4A. The structure of the microscope main body 1 itself is not limited to that shown in FIG. 1 either.

As explained above, by adopting the embodiment of the present invention, a liquid such as a reagent can be injected onto the specimen being observed without having to move the illumination device during the observation.

The above described embodiment is an example, and various modifications can be made without departing from the spirit and scope of the invention.

What is claimed is:

1. A microscope comprising:
   a stage on which a specimen container containing a specimen is placed;
   an illumination device disposed above the specimen, that illuminates the specimen;
   an objective lens disposed below the specimen, that forms an observation image by condensing light from the specimen illuminated with the illumination device;
   a pipette device that injects a liquid into the specimen container;
   a moving device that moves the pipette device between an injecting position at which the pipette device is engaged to inject the liquid into the specimen container and a retracted position at which the pipette device in not engaged in liquid injection; and
   an opening formed at the illumination device in an area that contains an optical axis of the objective lens and is surrounded by a plurality of light sources, that enables movement of the pipette device.

2. A microscope according to claim 1, wherein:
   the illumination device includes the plurality of light sources disposed to form a substantially ring shape along a circumference of a circle centering around the optical axis of the objective lens.

3. A microscope according to claim 2, further comprising:
   a phase plate disposed in the vicinity of a pupil of the objective lens; and
   the plurality of light sources are disposed at a position optically conjugate with the phase plate.

4. A microscope according to claim 1, wherein:
   the illumination device includes a plurality of light sources disposed to form a substantially ring shape along a circumference of a circle centering around an optical axis of the objective lens; and
   the opening is formed with an area containing the optical axis and surrounded by the plurality of light sources and a portion of the circle centering around the optical axis.

5. A microscope according to claim 4, further comprising:
   a phase plate disposed in the vicinity of a pupil of the objective lens; and
   the plurality of light sources are disposed at a position optically conjugate with the phase plate.

6. A microscope according to claim 1, wherein:
   the plurality of light sources of the illumination device includes a first light source group having a plurality of light sources disposed to form a substantially ring shape along a circumference of a circle centering around an optical axis of the objective lens and a second light source group having a plurality of light sources disposed further inward relative to the first light source group; and
   the microscope further comprises
   an illumination control unit that switches over between a first illumination mode in which the first light source group is turned on and the second light source group is turned off and a second illumination mode in which both the first light source group and the second light source group are turned on.

7. A microscope according to claim 6, further comprising:
   a phase plate disposed in the vicinity of a pupil of the objective lens; and
   the plurality of light sources are disposed at a position optically conjugate with the phase plate.

8. A microscope comprising:
   a stage on which a specimen container containing a specimen is placed;
   an illumination device disposed above the specimen, that illuminates the specimen;
   an objective lens disposed below the specimen, that forms an observation image by condensing light from the specimen illuminated with the illumination device;
   a pipette device that injects a liquid into the specimen container;
   a moving device that moves the pipette device between an injecting position at which the pipette device is engaged to inject the liquid into the specimen container and a retracted position at which the pipette device is not engaged in liquid injection; and
   an opening formed at the illumination device, that enables movement of the pipette device, wherein:
   the illumination device includes a plurality of light sources disposed over an entire area within a circle centering around an optical axis of the objective lens; and
   the opening is formed at an area inside the circle, which contains the optical axis.

9. A microscope according to claim 8, further comprising:
   a phase plate disposed in the vicinity of a pupil of the objective lens; and the plurality of light sources are disposed at a position optically conjugate with the phase plate.

10. A microscope comprising:

a stage on which a specimen container containing a specimen is placed;

an illumination device disposed above the specimen, that illuminates the specimen;

an objective lens disposed below the specimen, that forms an observation image by condensing light from the specimen illuminated with the illumination device;

a pipette device that injects a liquid into the specimen container;

a moving device that moves the pipette device between an injecting position at which the pipette device is engaged to inject the liquid into the specimen container and a retracted position at which the pipette device is not engaged in liquid injection; and an opening formed at the illumination device, that enables movement of the pipette device, wherein:

the illumination device includes a first light source group having a plurality of light sources disposed to form a substantially ring shape along a circumference of a circle centering around an optical axis of the objective lens and a second light source group having a plurality of light sources disposed further inward relative to the first light source group;

the opening is formed with a portion of an area containing the optical axis in which the second light source group is to be disposed and a portion of an area in which the first light source group is to be disposed; and the microscope further comprises an illumination control unit that switches over a first illumination mode in which the first light source group is turned on and the second light source group is turned off and a second illumination mode in which both the first light source group and the second light source group are turned on.

11. A microscope according to claim 10, further comprising:

a phase plate disposed in the vicinity of a pupil of the objective lens; and the plurality of light sources are disposed at a position optically conjugate with the phase plate.

* * * * *